United States Patent

Durette et al.

[11] 4,391,800
[45] Jul. 5, 1983

[54] IMMUNOLOGICALLY ACTIVE PEPTIDYL DISACCHARIDES AND METHODS OF PREPARATION

[75] Inventors: Philippe L. Durette, New Providence; Tsung-Ying Shen, Westfield, both of N.J.

[73] Assignee: Merck & Co., Inc., Rahway, N.J.

[21] Appl. No.: 33,597

[22] Filed: Apr. 27, 1979

[51] Int. Cl.³ ............... A61K 37/00; C07C 103/52
[52] U.S. Cl. ..................... 424/177; 260/112.5 R; 424/88
[58] Field of Search ............ 260/112.5 R; 536/1, 536/4, 53, 18; 424/177, 180, 88

[56] References Cited

U.S. PATENT DOCUMENTS

| | | | |
|---|---|---|---|
| 4,082,735 | 4/1978 | Jones et al. | 260/112.5 R |
| 4,082,736 | 4/1978 | Jones et al. | 260/112.5 R |
| 4,101,536 | 7/1978 | Yamamura et al. | 260/112.5 R |
| 4,101,649 | 7/1978 | Adams | 260/112.5 R |

FOREIGN PATENT DOCUMENTS

| | | |
|---|---|---|
| 852348 | 9/1977 | Belgium. |
| 852349 | 9/1977 | Belgium. |
| 2355505 | 1/1978 | France. |
| 52-2083506 | 7/1977 | Japan. |
| 52-2156812 | 12/1977 | Japan. |
| 53-3077011 | 7/1978 | Japan. |

OTHER PUBLICATIONS

Merser, C., et al., Tetrahedron Letters, No. 13, pp. 1029–1032, 1973.
Sharon, N., et al., J. Biol. Chem., vol. 241, pp. 223–241, 1966.
Ellouz, F., F., et al., Biochem. Biophys. Res. Comm. vol. 59, 1974, pp. 1317–1325.
Kusumoto, S., et al., Tetrahedron Letters, No. 45, pp. 4407–4410, 1978.
Bogdanov et al., FEBS Letters, vol. 57, No. 3, 259–261, 1975.
Adam, A., et al., Biochem. Biophys. Res. Comm., vol. 72, pp. 339–346, 1976.
Kotani, S., et al., Biken J., vol. 18, 105–111, 1975.

*Primary Examiner*—Blondel Hazel
*Attorney, Agent, or Firm*—Gabriel Lopez; Donald J. Perrella; Hesna J. Pfeiffer

[57] ABSTRACT

2-Amino-2-deoxy-β-$\underline{D}$-glucopyranosyl-(1-4)-2-amino-2-deoxy-$\underline{D}$-glucoses of the general structural formula:

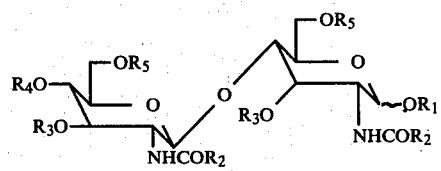

wherein
$R_1$ is hydrogen, alkyl (1–7C), substituted alkyl (1–7C), phenyl, substituted phenyl, benzyl, or substituted benzyl;
$R_2$ is alkyl, substituted alky, phenyl, or substituted phenyl and each $R_2$ may be the same group or a different group;
$R_3$ is H or

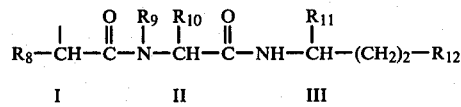

wherein
$R_8$ is H or lower alkyl (1–10C), and provided at least one of $R_3$ is not H,
$R_9$ is H, or $R_9$–$R_{10}$ together is —CH$_2$—CH$_2$—CH$_2$—;
$R_{10}$ is H, alkyl (L–7C), hydroxymethyl, mercaptomethyl, benzyl, or substituted benzyl;
$R_{11}$ and $R_{12}$ each is carboxyl, esterified carboxyl (1–7C), amidated carboxyl, or mono- or di-alkyl- (1–3C) amidated carboxyl;
$R_4$ and $R_5$ are the same or different and are H, aliphatic or aromatic acyl (2–21C) or substituted acyl (2–21C);
when $R_8$ is lower alkyl, the stereochemistry at asymmetric center I can be either $\underline{D}$ or $\underline{L}$;
when $R_{10}$ is not H, the stereochemistry at asymmetric center II is $\underline{L}$; the stereochemistry at asymmetric center III is $\underline{D}$.

These compounds possess immunostimulatory properties.

13 Claims, No Drawings

IMMUNOLOGICALLY ACTIVE PEPTIDYL DISACCHARIDES AND METHODS OF PREPARATION

BACKGROUND OF THE INVENTION

One of the most active immunoadjuvants is Freund's Complete Adjuvant which is a water-oil emulsion consisting of 10% Arlacel A and 90% mineral oil containing whole killed mycobacterial cells. A vaccine is formulated with Freund's Complete Adjuvant by incorporating the antigen in the aqueous phase. Therapeutic applications of Freund's Complete Adjuvant, however, have been prevented due to accompanying toxic side effects such as local granulomas, endotoxic shock, and adjuvant-induced polyarthritis. Subsequently, the minimal active structure of mycobacteria has been determined by Ellouz et al., Biochem. Biophys. Res. Commun., 59, 1317 (1974) and by Kotani et al., Biken J., 18, 105 (1975) to be a peptidoglycan fragment of the cell wall, more specifically, a muramyl dipeptide, namely, N-acetylmuramyl-$\underline{L}$-alanyl-$\underline{D}$-isoglutamine (MDP). The addition of synthetic MDP to an emulsion of Freund's incomplete adjuvant (90% mineral oil and 10% Arlacel A) containing an antigen increases the level of antibodies against the antigen (humoral response) and induces delayed hypersensitivity (cellular immunity).

The effects of various structural modifications of the dipeptidyl moiety of MDP on biological activity have been reported, although studies on the effects of modifications of the saccharide moiety, including oligosaccharide analogs, have been limited.

OBJECTS OF THE INVENTION

It is an object of the present invention to provide biologically active peptidyl disaccharides based on MDP having immunostimulatory properties. Another object is to provide methods for the preparation of these compounds. A further object is to provide formulations for incorporating these peptidyl disaccharides into a vaccine. These and other objects of the present invention will be apparent from the following description.

SUMMARY OF THE INVENTION

2-Amino-2-deoxy-$\beta$-$\underline{D}$-glucopyranosyl-(1→4)-2-amino-2-deoxy-$\underline{D}$-glucoses of the general structural formula:

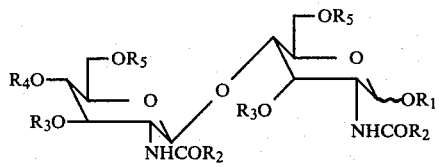

wherein
R$_1$ is hydrogen, alkyl (1–7C), substituted alkyl (1–7C), phenyl, substituted phenyl, benzyl, or substituted benzyl;
R$_2$ is alkyl, substituted alkyl, phenyl, or substituted phenyl and each R$_2$ may be the same group or a different group;
R$_3$ is H or

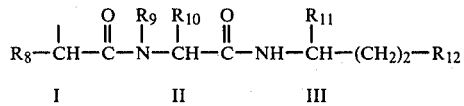

wherein
R$_8$ is H or lower alkyl (1–10C), and provided at least one of R$_3$ is not H,
R$_9$ is H, or R$_9$–R$_{10}$ together is —CH$_2$—CH$_2$—CH$_2$—
R$_{10}$ is H, alkyl (1–7C), hydroxymethyl, mercaptomethyl, benzyl, or substituted benzyl;
R$_{11}$ and R$_{12}$ each is carboxyl, esterified carboxyl (1–7C), amidated carboxyl, or mono- or dialkyl-(1–3C)amidated carboxyl;
R$_4$ and R$_5$ are same or different and are H, aliphatic or aromatic acyl (2–21C) or substituted acyl (2–21C);
when R$_8$ is lower alkyl, the stereochemistry at asymmetric center I can be either $\underline{D}$ or $\underline{L}$;
when R$_{10}$ is not H, the stereochemistry at asymmetric center II is $\underline{L}$; the
stereochemistry at asymmetric center III is D.

These compounds possess immunostimulatory properties.

The compounds of the present invention possess immunostimulatory properties and may be used as immunological adjuvants to stimulate the host immune response. They are especially useful for increasing the antigenicity of weakly immunogenic agents in vaccines against bacterial, viral, or parasitic infections or against various tissue antigens of normal or pathogenic origin. They can be used in place of whole killed mycobacterial cells in Freund's Complete Adjuvant. In addition, the compounds of the present invention when incorporated into a vaccine either as an aqueous or oil formulation lack the deleterious side effects observed in vaccine compositions containing Freund's Complete Adjuvant. Furthermore, the compounds of the present invention by themselves provide non-specific host protection against infectious organisms, for example, *Klebsiella pneumoniae, Candida albicans* or *Staphylococcus aureus*.

DETAILED DESCRIPTION

The prior art chemistry concerning MDP has been concerned, heretofore, mostly with modification of the dipeptidyl moiety, and no analog reported has proved to be more active than MDP itself. Studies on the effects of modification of the saccharide moiety, including oligosaccharide analogs, have been limited. The glycodipeptide moiety of the rigid polymeric bacterial cell wall peptidoglycan is composed of alternating units of $\beta$1→4 linked N-acetyl-$\underline{D}$-glucosamine (GlcNAc) and N-acetylmuramyl-$\underline{L}$-alanyl-$\underline{D}$-isoglutamine (muramyl dipeptide-MDP). Therefore, two structures are possible for the repeating disaccharide dipeptide unit of the peptidoglycan, one [MDP-($\beta$-1→4) GlcNAc] having N-acetyl-D-glucosamine and the other [GlcNAc-($\beta$1→4)-MDP] muramyl dipeptide at the reducing end of the $\beta$1→4 linked disaccharide. The present invention is concerned with immunostimulatory 2-amino-2-deoxy-$\beta$-$\underline{D}$-glucopyranosyl-(1→4)-2-amino-2-deoxy-$\underline{D}$-glucoses of the general structural formula 1:

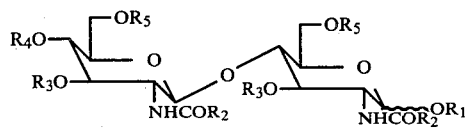
1 wherein
R$_1$ is hydrogen, alkyl (1–7C), substituted alkyl (1–7C), phenyl, substituted phenyl, benzyl, or substituted benzyl;

R$_2$ is alkyl, substituted alkyl, phenyl, or substituted phenyl and each R$_2$ may be the same group or a different group;

R$_3$ is H or

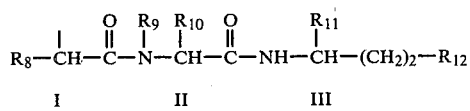

wherein
R$_8$ is H or lower alkyl (1–10C), and provided at least one of R$_3$ is not H, R$_9$ is H, or R$_9$-R$_{10}$ together is —CH$_2$—CH$_2$—CH$_2$—

R$_{10}$ is H, alkyl (1–7C), hydroxymethyl, mercaptomethyl, benzyl, or substituted benzyl;

R$_{11}$ and R$_{12}$ each is carboxyl, esterified carboxyl (1–7C), amidated carboxyl, or mono- or dialkyl-(1–3C)amidated carboxyl;

R$_4$ and R$_5$ are same or different and are H, aliphatic or aromatic acyl (2–21C) or substituted acyl (2–21C);

when R$_8$ is lower alkyl, the stereochemistry at asymmetric center I can be either $\underline{D}$ or $\underline{L}$;

when R$_{10}$ is not H, the stereochemistry at asymmetric center II is $\underline{L}$; the stereochemistry at asymmetric center III is $\underline{D}$.

These compounds possess immunostimulatory properties.

The compounds in the present invention possess immunostimulatory properties and may be used as immunological adjuvants to stimulate the host immune response. They are especially useful for increasing the antigenicity of weakly immunogenic agents in vaccines against bacterial, viral, or parasitic infections or against various tissue antigens of normal or pathogenic origin. They can be used in place of whole killed mycobacterial cells in Freund's Complete Adjuvant. In addition, the compounds of the present invention when incorporated into a vaccine either as an aqueous or oil formulation lack the deleterious side effects observed in vaccine compositions containing Freund's Complete Adjuvant. Furthermore, the compounds of the present invention by themselves provide non-specific host protection against infectious organisms, for example, *Klebsiella pneumoniae*, *Candida albicans* or *Staphylococcus aureus*.

The compounds of formula 1 may be prepared by condensing using conventional procedures, a protected compound of formula 2, 3, or 4 with a protected compound of formula 5, followed by removal of the protecting groups optionally present.

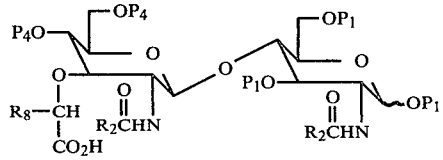
2

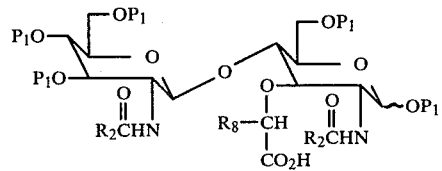
3

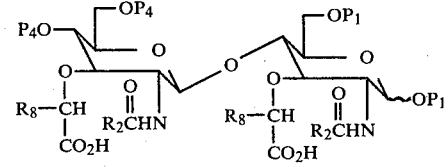
4

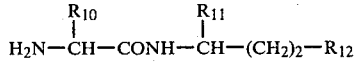
5

In the foregoing formulae, R$_2$, R$_8$, R$_{10}$, R$_{11}$ and R$_{12}$ represent the groups mentioned previously while P is a protecting group. The protecting group may be any suitable to protect the group to which it is attached during the condensation reaction and which may be readily removed thereafter. As protecting groups for the carboxyl group, there may be mentioned tertiary-butyl, benzyl or benzhydryl. For the hydroxyl groups, there may be mentioned the acyl radical, for example, the alkanoyl radical, such as acetyl, the aroyl radical, such as benzoyl, and, in particular, radicals derived from carbonic acid, such as benzyloxycarbonyl or lower alkyloxycarbonyl. Also to be mentioned are alkyl radicals, such as tertiary-butyl, benzyl, nitrobenzyl, lower alkoxy radical, or the tetrahydropyranyl radical. In addition, there may be mentioned the optionally substituted alkylidene radicals that block the oxygen atoms at the C-4 and C-6 positions. Among the alkylidene radicals, one finds, in particular, the lower alkylidene radicals, especially ethylidene, isopropylidene, or propylidene, and also, the optionally substituted benzylidene radical, preferentially substituted at the para position. For a more complete listing of protecting groups, reference may be had to standard works on peptide chemistry, e.g. Bodanszky et al., "Peptide Synthesis", chapter 4, Interscience Publishers, 1966 or Schroeder et al., "The Peptides" Vol. I, pp. xxiii-xxix, Academic Press, 1965, and to the text, "Protective Groups in Organic Chemistry", Plenum Press, 1973, J. F. W. McOmie, (ed.).

The condensation is effected by reacting the compound 2, 3, or 4 in the form where the carboxylic acid is activated with the amino compound 5. The activated carboxyl group may be, for example, an acid anhydride, preferably, a mixed acid anhydride like an acetate of the acid, an amide of the acid like an imidazolid, an isoxazolid or an activated ester. The activated esters, include the cyanomethyl ester, the carboxylmethyl ester, the p-nitrophenyl thioester, the p-nitrophenyl ester, the 2,4,5-trichlorophenyl ester, the pentachlorophenyl ester, the N-hydroxysuccinimide ester, the N-hydroxyphthalimide ester, the 8-hydroxyquinoline ester, the 2-hydroxy-1,2-dihydro-1-carboethoxyquinoline esters, the N-hydroxypiperidine ester or enol ester derived from N-ethyl-5-phenyl-isoxazolium-3'-sulfonate. The activated esters may equally be obtained from a carbodiimide by addition of N-hydroxysuccinimide or from a substituted 1-hydroxybenzyltriazole for example, a halogen, methyl, or methoxy-substituted 3-hydroxy-4-oxo-3,4-dihydrobenzo-[d]-1,2,3-triazine.

The amino group may be activated, for example, by reaction with a phosphitamide.

Among the methods of reaction with the activated esters, one must mention in particular those that involve N-ethyl-5-phenyl-isoxazolium-3'-sulfonate (Woodward's Reagent K), N-ethoxycarbonyl-2-ethoxy-1,2-dihydroquinoline, or carbodiimide. Upon completion of the coupling reaction, the protecting groups may be removed in conventional manner to yield a compound of formula 1.

The compounds of formulae 2, 3, and 4 can be obtained by reacting the corresponding sugar unsubstituted at position-3' (compound of formula 6), position-3 (compound of formula 7), or positions -3,3' (compound of formula 8), respectively, with a halogen-$R_8$-acetic acid where $R_8$ has the meaning mentioned above. The ether is obtained in the presence of a strong base. The halogen is preferentially bromo or chloro. Compounds of formula 5 are known or can be made in a known fashion by coupling the appropriately protected amino acids, and removing protecting groups.

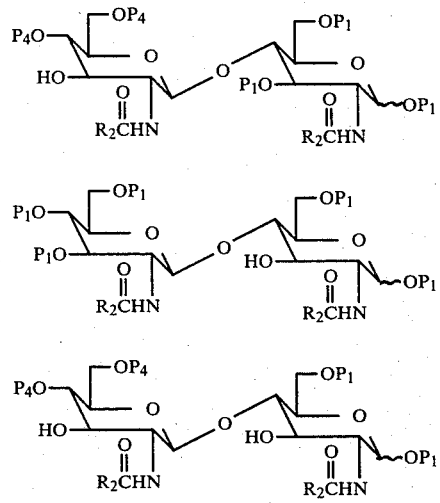

Compounds of formula 6 can be obtained by condensing a protected compound of formula 9, wherein X is halogen, preferably bromo or chloro, with a protected compound of formula 10 to give compounds of formula 11, where $R_2$ has the meaning mentioned above.

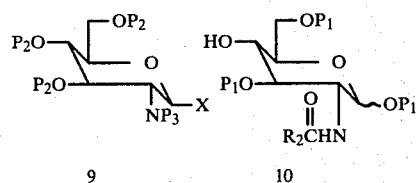

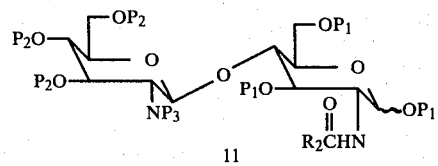

The condensation is effected by reacting compounds 9 and 10 under conditions effective to liberate hydrogen halide. $P_1$, $P_2$ and $P_3$ are readily removable but different protecting groups where $P_2$ and $P_3$ are readily removable under conditions which do not remove the $P_1$ group. $P_3$ is an imido protecting group. The $P_2$ and $P_3$ protecting groups are then selectively removed; the liberated amino group at position C-2' is then acylated to insert the group $$\underset{\displaystyle C-R_2;}{\overset{\displaystyle O}{\|}}$$

and the C-4' and C-6' hydroxyls blocked with protecting group $P_4$ to give compounds of formula 6.

Compounds of formula 7 can be obtained by condensing a protected compound of formula 9, wherein X is halogen, preferably bromo or chloro, with a protected compound of formula 12, to give compounds of formula 13, where $R_2$ has the meaning mentioned above. $P_1$, $P_2$, $P_3$ and $P_5$ are readily removable but different protecting groups where $P_2$ and $P_3$ are readily removable under conditions which do not remove $P_1$ and $P_5$, and $P_5$ selectively removable under conditions which do not remove $P_1$.

$P_3$ is an imido protecting group. The $P_2$ and $P_3$ protecting groups are then selectively removed; the liberated amino group at position C-2' is then acylated to insert the group $$\underset{\displaystyle C-R_2;}{\overset{\displaystyle O}{\|}}$$

the C-3', C-4', and C-6' hydroxyls blocked with protecting group $P_1$; and the $P_5$ protecting group selectively removed to give compounds of formula 7.

Compounds of formula 8 can be obtained by condensing a protected compound of formula 9 with a protected compound of formula 12, where the various protecting groups have the meaning mentioned above, to give the compounds of formula 13. The $P_5$ protecting group is then selectively removed; the $P_2$ and $P_3$ protecting groups are next removed; the liberated amino group at position C-2' is then acylated to insert the group

and the C-4' and C-6' hydroxyls blocked with protecting group $P_4$ to give compounds of formula 8.

The protecting groups can be removed in a classical fashion, for example, by hydrogenolysis with hydrogen in the presence of a noble metal catalyst, such as palladium or platinum, or by acid hydrolysis.

In any of the foregoing methods for the synthesis of the compounds of the present invention, when $R_4$ and $R_5$ are greater than acetyl, the desired group is obtained by employing the appropriate acid anhydride or acid halide, preferably the acid chloride, e.g. propionyl chloride, when $R_4$ and $R_5$ are propionyl. When $R_4$ is H and $R_5$ is acyl, it is not necessary to protect $R_4$. However, when $R_5$ is hydrogen and $R_4$ is acyl, then $R_5$ must be protected, preferably with trityl ether, before acylating $R_4$ followed by deblocking $R_5$. Compounds wherein $R_{10}$ is other than methyl, may be obtained when, for example, one of the following amino acids is substituted for alanine:

| Amino acid | $R_{10}$ |
|---|---|
| serine | $CH_2OH$ |
| cysteine | $CH_2SH$ |
| phenylalanine | benzyl |
| tyrosine | p-hydroxybenzyl |
| valine | isopropyl |
| leucine | 2-methylpropyl |
| isoleucine | 1-methylpropyl |
| α-aminobutyric | $CH_2CH_3$ |
| norvaline | $CH_2CH_2CH_3$ |
| norleucine | $CH_2CH_2CH_2CH_3$ |

Compounds wherein $R_9$ and $R_{10}$ together are $-CH_2CH_2CH_2-$ are obtained by substituting proline for alanine.

The term "substituted alkyl" for $R_1$ and $R_2$ refers to an alkyl group of from 1 to 7 carbon atoms substituted by hydroxy, mercapto, alkoxy of 1-3 carbons, alkylmercapto of 1-3 carbons, hydroxy or mercapto esterified by an acid of 1-4 carbon atoms, halogen (F, Cl or Br), carboxyl, or carboxyl functionally modified by esterification with a lower alcohol of 1-3 carbons or by amidation. Preferably the alkyl substituents are hydroxy or mercapto, either free or substituted by an alkyl group of 1-3 carbons.

The substituents in the terms "substituted phenyl" for $R_1$ and $R_2$ or "substituted benzyl" for $R_1$ refer to the phenyl group substituted by one or more alkyl groups of 1-3 carbon carbons or hydroxy or mercapto groups either free, or etherified by an alkyl group of 1-3 carbons or esterified by an acid of 1-4 carbons, lower (1-4C) alkyldioxy, cycloalkyldioxy of 5-7 carbon atoms, amino or trifluoromethyl.

The acyl group for $R_4$ and $R_5$ represents an alkanoyl or optionally substituted alkanoyl radical and especially an alkanoyl comprising 2 to 21 carbon atoms, like acetyl or propionyl, and also an aroyl like benzoyl, naphthoyl-1 and naphthoyl-2, and, in particular, benzoyl or naphthoyl substituted with halogen, lower alkyl (1-3C), lower alkoxy (1-3C), trifluoromethyl, hydroxy, or lower alkanoyloxy. Acyl also represents a sulfonyl radical of an organic sulfonic acid like alkanesulfonic acid, in particular, a lower alkanesulfonic acid, like methanesulfonic acid or ethanesulfonic acid or an arylsulfonic acid, in particular, a phenylsulfonic acid optionally substituted by a lower alkyl, like benzenesulfonic acid or p-toluenesulfonic acid. Acyl also represents a carbamoyl radical, like a non-substituted carbamoyl, a lower (1-3C) alkylcarbamoyl or arylcarbamoyl, like the methylcarbamoyl or the phenylcarbamoyl.

For $R_{11}$ and $R_{12}$, among the optionally esterified carboxyl groups can be mentioned the carboxyl group esterified by a lower alcohol of 1-7 carbons, like methanol or ethanol. The carboxyl group can also be amidated, unsubstituted at the nitrogen atom or mono- or di-substituted with an alkyl, in particular, a lower alkyl, an aryl, particularly phenyl, or an aralkyl, particularly benzyl.

Most preferably, $R_1$ is H, alkyl of 1-3 carbons, benzyl, phenyl or phenyl p-substituted by alkyl (1-3C), amino, halogen, hydroxy or trifluoromethyl; $R_2$ is alkyl of 1-3 carbons, or phenyl, or phenyl p-substituted by alkyl (1-3C), amino, halogen, hydroxy or trifluoromethyl; $R_3$ is H or lower alkyl of 1-3 carbons, $R_4$ and $R_5$ are H, alkanoyl of 2-21 carbons, benzoyl or naphthoyl; $R_{10}$ is H, alkyl of 1-4 carbons, hydroxymethyl, mercaptomethyl, benzyl or p-hydroxybenzyl; $R_9$ and $R_{10}$ together are $-CH_2CH_2CH_2-$; and $R_{11}$ and $R_{12}$ are carboxyl, carboxyl esterified by an alcohol of 1-4 carbons, carboxamide, or monoalkyl or dialkyl substituted carboxamide wherein the alkyl group has from 1-3 carbons.

The obtained compounds can be transformed to their salts in a classical fashion, for example, by reacting the acidic compounds obtained with alkaline or alkaline earth hydroxides or the basic compounds with acids.

The present invention is also directed to pharmaceutical preparations that contain a compound of formula 1. Among the pharmaceutical preparations relevant to this invention are salts that are administered by external route, for example, orally, rectally or parenterally to mammalian species. Preparations may be administered that contain the pharmacologically active compound by itself or mixed with a pharmaceutically acceptable carrier. The dose of the pharmacologically active compound depends on the animal specie, the age, and the state of the individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

The immunostimulatory properties of the compounds in the present invention can be demonstrated with the following protocols:

1. In vivo Stimulation of Humoral Response: Increase in the Production of Antibodies Against Bovine Serum Albumin (BSA) in the Mouse Mice (NMRI) are immunized by i.p. injections of 10 mg of BSA without precipitate. At 0, 9, 15 and 29 days later blood samples are taken and analyzed for anti-BSA-antibody titers by the passive hemagglutination technique. At the dose utilized, soluble BSA is subimmunogenic for the receiving animals, that is, it does not cause any antibody production, or at most a completely insignificant production. Additional treatment of the mice with certain immunostimulants before or after administration of antigen leads to an increase in antibody titer in the serum. The effect of the treatment is expressed by the obtained score, that is, the sum of the logs to the base 2 of the differences of the titer at 3 days of bleeding.

The compounds of the present invention are capable of augmenting in a significant manner the production of anti-BSA antibodies by i.p. or subcutaneous application (s.c.) of 100-300 mg/kg/animal during 5 consecutive days (day 0 to day 4) after immunization with BSA.

The immunostimulatory effect of the compounds mentioned herein depend on the antigen, contrary to other bacterial immunostimulants (like LPS of E. coli). The injection of the compounds of the present invention results in augmentation of anti-BSA antibody titer only in mice immunized with BSA, and not with nonimmunized mice. Subcutaneous administration is as efficacious as i.p., that is, the immunostimulatory effect observed is systemic and does not depend on the fact that the stimulant was administered by the same route as the antigen or mixed with it, as is the case with classical adjuvants.

The compounds of the present invention permit specific augmentation of humoral immunity, improve immune response, and provide long-lasting immunostimulatory effects on systemic activation of immune apparatus.

2. Stimulation of Mitotic Responses of Lymphocyte Cultures

Mouse lymphoid cells are cultured in microtiter plates, in RPMI-1640 medium with 2% fetal calf serum. Cultures are set in triplicates and consist of $3-5\times 10^5$ spleen or $1.5\times 10^6$ thymus cells per well in a final volume of 0.2 ml. Class specific mitogens are added at optimal or suboptimal concentrations, while control cultures are incubated without mitogens. The tested compounds are added shortly after the mitogens and the cultures are incubated for 48 hours at 37° with 5% $CO_2$. Incorporation of tritiated thymidine is determined after a pulse (1.0 $\mu$Ci/well) during the last 6 hours in culture. The data are recorded as mean cpm and the effects of the compounds are presented as stimulation index (mean cpm in cultures with the compound/mean cpm in control).

The compounds of the present invention enhance the levels of thymidine incorporation in lymphocyte cultures, with or without mitogens. The stimulation indices are maximal in control cultures or in those with suboptimal doses of mitogens. Similar effects of the compound are provoked in cultures of different lymphocyte populations, namely, B cells (nude spleen), T cells (thymus) or their mixtures (normal spleen). The effects of the compounds are dose-dependent. These compounds, therefore, are capable of stimulating proliferation of lymphocytes that participate in the humoral response (B cells) as well as in cellular immunity (T cells).

3. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds of the present invention thus have the capacity, on the one hand, of being mixed with an antigen for which an increase in immunogenicity is required and on the other hand, by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as (1) adjuvants by mixing them with vaccines with the goal of improving the effectiveness of the vaccination and (2) protective agents against infections caused by bacteria, viruses or pathogenic parasites, owing to immunity by humoral antibodies and/or to cellular mediation.

Thus, the described compounds are indicated, mixed with the most varied antigens, as adjuvants for experimental as well as industrial production of antisera for therapeutic and diagnostic purposes, as well as to induce immunologically active lymphocyte populations at the time of cell transfers.

Moreover, one can equally utilize the new compounds without simultaneously supplying antigen in order to enhance immune reactions that are already taking place in a subliminal fashion in a mammalian host. These compounds are therefore especially indicated for stimulation of individual immune defense, e.g., at the time of chronic or acute infections or in cases of selective (antigen-specific) immunological deficiencies as well as in situations of immune deficiency, but also acquired general deficiency (i.e., not antigen-specific) as appears with age, during initial shock from a grave illness, and before and soon after radiation therapy or immunosuppressive hormones. The said compounds can subsequently be administered in combination with antiinfectious antibiotics, chemical therapeutics or other methods of treatment, to combat immunological deficiencies. The described compounds are thus indicated equally for general prophylaxis of infectious disease in man and animal.

The following examples illustrate the present invention without, however, limiting the same thereto. All temperatures are expressed in degrees Celsius.

EXAMPLE 1

Preparation of 2-acetamido-4-O-[2-acetamido-2-deoxy-3-O-(D-2-propionyl-L-alanyl-$\underline{D}$-isoglutamine)-$\beta$-$\underline{D}$-glucopyranosyl]-2-deoxy-$\underline{D}$-glucopyranose Step A: Preparation of benzyl 2-acetamido-4-O-(3,4,6-tri-O-acetyl-2-deoxy-2-phthalimido-$\beta$-$\underline{D}$-glucopyranosyl)-3,6-di-O-benzyl-2-deoxy-$\alpha$-$\underline{D}$-glucopyranoside To a solution of benzyl 2-acetamido-3,6-di-O-benzyl-2-deoxy-$\alpha$-$\underline{D}$-glucopyranoside [prepared by the process set forth in J. C. Jacquinet, et al., Carbohydr. Res., 38, 305 (1974)] (2.95 g, 6.00 mmol), silver trifluoromethanesulfonate (triflate) (1.90 g, 7.39 mmol), and 2,4,6-collidine (0.90 g, 7.42 mmol) in dry nitromethane (45 ml) stirred at room temperature under an atmosphere of nitrogen is added a solution of 3,4,6-tri-O-acetyl-2-deoxy-2-phthalimido-$\beta$-$\underline{D}$-glucopyranosyl chloride [prepared by the process set forth in S. Akiya et al., Chem. Pharm. Bull., 8, 583 (1960)](3.35 g, 7.38 mmol) in dry nitromethane (45 ml). After stirring for 6 hours at room temperature, additional chloride (1.73 g, 3.81 mmol), silver triflate (0.98 g, 3.81 mmol), and collidine (0.46 g, 3.80 mmol) are added, and stirring is continued overnight with exclusion of moisture. The mixture is then diluted with chloroform (150 ml), undissolved solids removed by filtration, and the filter washed with chloroform (60 ml). The combined filtrates are washed successively with cold water, 3% aqueous hydrochloric acid, saturated aqueous sodium bicarbonate, and water. The dried (sodium sulfate) organic solution is evaporated and the resulting syrup is treated for 6 hours with acetic anhydride (30 ml) and pyridine (40 ml). The mixture is then evaporated and coevaporated several times with toluene. The residue is dissolved in the minimal volume of dichloromethane and the solution applied to a column of silica gel (E. Merck, No. 7734, 70–230 mesh) (900 g packed as a slurry in 9:1 dichloromethane-diethyl ether). Elution with 90:10:0.25 dichloromethane-diethyl ether-methanol and evaporation of the appropriate fractions affords benzyl 2-acetamido-4-O-(3,4,6-tri-O-acetyl-2-deoxy-2-phthalimido-$\beta$-D-glucopyranosyl)-3,6-di-O-benzyl-2-deoxy-$\alpha$-D-glucopyranoside as an amorphous solid; yield 2.17 g (39.8%), $[\alpha]_D^{25}$ +57.1° (c, 1, chloroform). The 300-MHz nmr spectrum in chloroform-d is in accord with the desired structure.

Step B: Preparation of benzyl
2-acetamido-4-O-(2-acetamido-2-deoxy-$\beta$-D-glucopyranosyl)-3,6-di-O-benzyl-2-deoxy-$\alpha$-D-glucopyranoside A solution of benzyl 2-acetamido-4-O-(3,4,6-tri-O-acetyl-2-deoxy-2-phthalimido-$\beta$-D-glucopyranosyl)-3,6-di-O-benzyl-2-deoxy-$\alpha$-D-glucopyranoside (2.1 g, 2.3 mmol) in methanol (80 ml) and n-butylamine (20 ml) is heated for 48 hours at reflux temperature. Cooling and evaporation of the reaction mixture gives a solid that is slurried in water and lyophilized. The resulting solid is dissolved in the minimal volume of N,N-dimethylformamide and the solution applied to a column of silica gel (E. Merck, No. 7734, 70–230 mesh). Elution with 20:1 chloroform-methanol and evaporation of the appropriate fractions gives a chromatographically homogeneous solid that is dissolved in methanol (35 ml) and treated with acetic anhydride (2.5 ml) for 2 hours at room temperature. Evaporation of the reaction mixture and several coevaporations with toluene gives a solid that is crystallized from ethanol to afford pure benzyl 2-acetamido-4-O-(2-acetamido-2-deoxy-$\beta$-D-glucopyranosyl)-3,6-di-O-benzyl-2-deoxy-$\alpha$-D-glucopyranoside; yield 1.1 g (69%), m.p. 252°–256° (dec.), $[\alpha]_D^{25}$ +72° (c, 1.2, methanol). The 300-MHz nmr spectrum in methanol-d$_4$ is in accord with the desired structure.

Step C: Preparation of benzyl
2-acetamido-4-O-(2-acetamido-4,6-O-benzylidene-2-deoxy-$\beta$-D-glucopyranosyl)-3,6-di-O-benzyl-2-deoxy-$\alpha$-D-glucopyranoside A mixture of benzyl 2-acetamido-4-O-(2-acetamido-2-deoxy-$\beta$-D-glucopyranosyl)-3,6-di-O-benzyl-2-deoxy-$\alpha$-D-glucopyranoside (821 mg, 1.18 mmol) and freshly fused zinc chloride (800 mg) in benzaldehyde (12 ml) is stirred overnight at room temperature with exclusion of moisture. Water and hexane are then added to the reaction mixture and, after stirring for 1 hour, the resulting solid is filtered, washed extensively with water and then hexane. Recrystallization from methanol affords pure benzyl 2-acetamido-4-O-(2-acetamido-4,6-O-benzylidene-2-deoxy-$\beta$-D-glucopyranosyl)-3,6-di-O-benzyl-2-deoxy-$\alpha$-D-glucopyranoside; yield 830 mg (90%), m.p. 298°–302° (dec), $[\alpha]_D^{25}$ +58.2° (c, 1.1, N,N-dimethylformamide). The 300-MHz nmr spectrum in chloroform-d is in accord with the desired structure.

Step D: Preparation of benzyl
2-acetamido-4-O-[2-acetamido-4,6-O-benzylidene-3-O-(D-1-carboxyethyl)-2-deoxy-$\beta$-D-glucopyranosyl]-3,6-di-O-benzyl-2-deoxy-$\alpha$-D-glucopyranoside To a stirred solution of benzyl 2-acetamido-4-O-(2-acetamido-4,6-O-benzylidene-2-deoxy-$\beta$-D-glucopyranosyl) (429 mg, 0.55 mmol) in dry p-dioxane (30 ml) is added sodium hydride in oil suspension (125 mg) (50% of sodium hydride by weight). The mixture is kept for 1 hour at 95°, the temperature decreased to 65°, and a solution of L-2-chloropropionic acid (120 mg, 1.11 mmol) in a small volume of dry p-dioxane added. After 1 hour at 65°, additional sodium hydride (500 mg) is added, and the stirring is continued overnight at 65°. To the cooled reaction mixture, water (7.5 ml) is carefully added dropwise to decompose excess sodium hydride. The mixture is transferred to a separatory funnel, the lower alkaline dark-colored layer discarded, the upper organic layer filtered and partially concentrated. Dilution with water (5 ml) and chloroform gives a solid that is filtered and washed with diethyl ether. The chloroform layer of the filtrate is extracted once with water, and the combined aqueous layers are acidified at 0° with 2.5 M hydrochloric acid to pH 3. Several extractions with chloroform followed by drying (sodium sulfate) of the combined organic extracts and evaporation give additional product. The combined solids are reprecipitated with methanol-diethyl ether to afford pure benzyl 2-acetamido-4-O-[2-acetamido-4,6-O-benzylidene-3-O-(D-1-carboxyethyl)-2-deoxy-$\beta$-D-glucopyranosyl]3,6-di-O-benzyl-2-deoxy-$\alpha$-D-glucopyranoside as an amorphous white solid; yield 426 mg (91%), $[\alpha]_D^{25}$ +45° (c, 1, methanol). The 300-MHz nmr spectrum in dimethyl sulfoxide-d$_6$ is in accord with the desired structure.

Step E: Preparation of benzyl
2-acetamido-4-O-[2-acetamido-4,6-O-benzylidene-2-deoxy-3-O-(D-2-propionyl-L-alanyl-D-isoglutamine benzyl
ester)-$\beta$-D-glucopyranosyl]3,6-di-O-benzyl-2-deoxy-$\alpha$-D-glucopyranoside To a solution of benzyl 2-acetamido-4-O-[2-acetamido-4,6-O-benzylidene-3-O-(D-1-carboxyethyl)-2-deoxy-$\beta$-D-glucopyranosyl]-3,6-di-O-benzyl-2-deoxy-$\alpha$-D-glucopyranoside (216 mg, 0.25 mmol) in dry N,N-dimethylformamide (25 ml) at $-15°$ are added successively N-methylmorpholine (28 $\mu$l) and isobutyl chloroformate (33 $\mu$l). After stirring for 3 minutes at $-15°$, a precooled solution of L-alanyl-D-isoglutamine benzyl ester hydrochloride (102 mg, 0.30 mmol) and N-methylmorpholine (33 $\mu$l) in dry N,N-dimethylformamide (25 ml) is added. The mixture is then stirred for 4 hours at $-15°$ with exclusion of moisture. After the temperature is increased to 0°, 2.5 M aqueous potassium hydrogencarbonate (1 ml) is added, and the mixture is stirred for 30 minutes at 0° and then poured into water (25 ml). The precipitated solid is filtered, washed with water, dried by suction, washed with diethyl ether, and finally dried in vacuo at 50° over phosphorous pentoxide; yield 270 mg (93%), m.p. 295°–300° (dec), $[\alpha]_D^{25}$ +59.3° (c, 0.54, N,N-dimethylformamide). The 300 MHz nmr spectrum in dimethylsulfoxide-d$_6$ is in accord with the desired structure.

Step F: Preparation of 2-acetamido-4-O-[2-acetamido-2-deoxy-3-O-(D-2-propionyl-L-alanyl-D-isoglutamine)-β-D-glucopyranosyl]-2-deoxy-D-glucopyranose A solution of benzyl 2-acetamido-4-O-[2-acetamido-4,6-O-benzylidene-2-deoxy-3-O-(D-2-propionyl-L-alanyl-D-isoglutamine benzyl ester)-β-D-glucopyranosyl]-3,6-di-O-benzyl-2-deoxy-α-D-glucopyranoside (30 mg) in glacial acetic acid (5 ml) is hydrogenolyzed at atmospheric pressure in the presence of 10% palladium-on-charcoal (50 mg) for 24 hours at room temperature. Additional catalyst (25 mg) is then added and hydrogenolysis is continued for another 24 hours. The catalyst is removed by filtration through Celite and washed with acetic acid. The combined filtrates are evaporated, coevaporated several times with water, and finally several times with toluene. The residue is dissolved in the minimal volume of a methanol-ethanol mixture and the product precipitated by addition of diethyl ether. The solid is filtered, dissolved in a small volume of water, and lyophilized to afford 2-acetamido-4-O-[2-acetamido-2-deoxy-3-O-(D-2-propionyl-L-alanyl-D-isoglutamine)-β-D-glucopyranosyl]-2-deoxy-D-glucopyranose as a white amorphous solid; yield 17.3 mg (95%). The 300 MHz nmr spectrum in deuterium oxide is in accord with the desired structure.

EXAMPLE 2

Preparation of 2-acetamido-4-O-[2-acetamido-4,6-di-O-acetyl-2-deoxy-3-O-(D-2-propionyl-L-alanyl-D-isoglutamine)-β-D-glucopyranosyl]-2-deoxy-D-glucopyranose Step A: Preparation of benzyl 2-acetamido-4-O-[2-acetamido-2-deoxy-3-O-(D-2-propionyl-L-alanyl-D-isoglutamine benzyl ester)-β-D-glucopyranosyl]-3,6-di-O-benzyl-2-deoxy-α-D-glucopyranoside A mixture of benzyl 2-acetamido-4-O-[2-acetamido-4,6-O-benzylidene-2-deoxy-3-O-(D-2-propionyl-L-alanyl-D-isoglutamine benzyl ester)-β-D-glucopyranosyl]-3,6-di-O-benzyl-2-deoxy-α-D-glucopyranoside (68 mg) in 70% aqueous acetic acid (12 ml) is stirred for 2 hours at 80°. The solution is then evaporated and coevaporated several times with toluene. The residue is dissolved in the minimal volume of N,N-dimethylformamide and the solution applied to a column of silica gel (E. Merck, No. 7734, 70–230 mesh). Elution with 20:1 chloroform-methanol and evaporation of the appropriate fractions gives pure benzyl 2-acetamido-4-O-[2-acetamido-2-deoxy-3-O-(D-2-propionyl-L-alanyl-D-isoglutamine benzyl ester)-β-D-glucopyranosyl]-3,6-di-O-benzyl-2-deoxy-α-D-glucopyranoside as a white solid, yield, 23 mg (37%). The 300 MHz nmr spectrum in dimethyl sulfoxide-d$_6$ is in accord with the desired structure.

Step B: Preparation of benzyl 2-acetamido-4-O-[2-acetamido-4,6-di-O-acetyl-2-deoxy-3-O-(D-2-propionyl-L-alanyl-D-isoglutamine benzyl ester)-β-D-glucopyranosyl]-3,6-di-O-benzyl-2-deoxy-α-D-glucopyranoside A solution of benzyl 2-acetamido-4-O-[2-acetamido-2-deoxy-3-O-(D-2-propionyl-L-alanyl-D-isoglutamine benzyl ester)-β-D-glucopyranosyl]-3,6-di-O-benzyl-2-deoxy-α-D-glucopyranoside (21 mg) in N,N-dimethylformamide (0.3 ml) is treated with acetic anhydride (0.1 ml) and pyridine (0.2 ml) overnight at room temperature. The mixture is then evaporated and traces of pyridine removed by several coevaporations with toluene. Pure benzyl 2-acetamido-4-O-[2-acetamido-4,6-di-O-acetyl-2-deoxy-3-O-(D-2-propionyl-L-alanyl-D-isoglutamine benzyl ester)-β-D-glucopyranosyl]-3,6-di-O-benzyl-2-deoxy-α-D-glucopyranoside is obtained as a white solid; yield 21 mg (93%). The 300 MHz nmr spectrum in dimethyl sulfoxide-d$_6$ is in accord with the desired structure.

Step C: Preparation of 2-acetamido-4-O-[2-acetamido-4,6-di-O-acetyl-2-deoxy-3-O-(D-2-propionyl-L-alanyl-D-isoglutamine)-β-D-glucopyranosyl]-2-deoxy-D-glucopyranose A solution of benzyl 2-acetamido-4-O-[2-acetamido-4,6-di-O-acetyl-2-deoxy-3-O-(D-2-propionyl-L-alanyl-D-isoglutamine benzyl ester)-β-D-glucopyranosyl]-3,6-di-O-benzyl-2-deoxy-α-D-glucopyranoside (20 mg) in glacial acetic acid (5 ml) is hydrogenolyzed at atmospheric pressure in the presence of palladium black (50 mg) for 48 hours at room temperature. The catalyst is removed by filtration through Celite and washed with acetic acid. The combined filtrates are evaporated, coevaporated several times with water, and finally several times with toluene. The residue is dissolved in a small volume of water and lyophilized to afford 2-acetamido-4-O-[2-acetamido-4,6-di-O-acetyl-2-deoxy-3-O-(D-2-propionyl-L-alanyl-D-isoglutamine)-β-D-glucopyranosyl]-2-deoxy-D-glucopyranose as a white amorphous solid, yield 12.6 mg (92%). The 300 MHz nmr spectrum in deuterium oxide is in accord with the desired structure.

EXAMPLE 3

Preparation of 2-acetamido-4-O-(2-acetamido-2-deoxy-β-D-glucopyranosyl)-2-deoxy-3-O-(D-2-propionyl-L-alanyl-D-isoglutamine)-D-glucopyranose Step A: Preparation of benzyl 2-acetamido-4-O-(3,4,6-tri-O-acetyl-2-deoxy-2-phthalimido-β-D-glucopyranosyl)-3-O-allyl-6-O-benzyl-2-deoxy-α-D-glucopyranoside To a solution of benzyl 2-acetamido-3-O-allyl-6-O-benzyl-2-deoxy-α-D-glucopyranoside [prepared by the process set forth in J. C. Jacquinet & P. Sinäy, J. Org. Chem., 42, 720 (1977)] (2.34 g, 5.30 mmol), silver trifluoromethanesulfonate (1.67 g, 6.50 mmol), and 2,4,6-collidine (0.86 ml, 6.5 mmol) in dry nitromethane (27 ml) stirred at room temperature under an atmosphere of nitrogen is added a solution of 3,4,6-tri-O-acetyl-2-deoxy-2-phthalimido-β-D-glucopyranosyl chloride [prepared by the process set forth in S. Akiya et al., Chem. Pharm. Bull., 8, 583 (1960)] (2.89 g, 6.37 mmol) in dry nitromethane (15 ml). After stirring for 5 hours at room temperature, additional chloride (1.22 g, 2.69 mmol), silver trifluoromethanesulfonate (0.74 g, 2.9 mmol), and collidine (0.38 ml, 2.9 mmol) are added, and stirring is continued overnight with exclusion of moisture. The mixture is then diluted with chloroform (120 ml), undissolved solids removed by filtration, and the filter washed with chloroform (40 ml). The combined filtrates are washed with cold water, 3% aqueous hydrochloric acid, saturated aqueous sodium bicarbonate, and water. The dried (sodium sulfate) organic solution is evaporated, and the resulting syrup is treated for 3 hours at 0° with acetic anhydride (40 ml) and pyridine (60 ml). The mixture is then evaporated and coevaporated several times with toluene. The mixture is separated on dual Prep-Pak® 500 silica gel columns using a Waters Associates Prep Liquid Chromatography System 500 with 9:1 diethyl ether-dichloromethane as eluant. Benzyl 2-acetamido-4-O-(3,4,6-tri-O-acetyl-2-deoxy-2-phthalimido-$\beta$-D-glucopyranosyl)-3-O-allyl-6-O-benzyl-2-deoxy-$\alpha$-D-glucopyranoside is obtained as a chromatographically homogeneous amorphous solid; yield 1.72 g (38%), $[\alpha]_D^{25}+50°$ (c, 1.2, chloroform). The 300-MHz nmr spectrum in chloroform-d is in accord with the desired structure.

Step B: Benzyl 2-acetamido-4-O-(2-acetamido-2-deoxy-$\beta$-D-glucopyranosyl)-3-O-allyl-6-O-benzyl-2-deoxy-$\alpha$-D-glucopyranoside A solution of benzyl 2-acetamido-4-O-(3,4,6-tri-O-acetyl-2-deoxy-2-phthalimido-$\beta$-D-glucopyranosyl)-3-O-allyl-6-O-benzyl-2-deoxy-$\alpha$-D-glucopyranoside (952 mg, 1.11 mmol) in methanol (32 ml) and n-butylamine (8 ml) is heated for 48 hours at reflux temperature. Cooling and evaporation of the reaction mixture give a solid that is slurried in water and lyophilized. The resulting solid is dissolved in the minimal volume of methanol and the solution applied to a column of silica gel (70 g). Elution with 14:1 chloroform-methanol and evaporation of the appropriate fractions give a chromatographically homogeneous solid (537 mg) that is dissolved in methanol (20 ml) and treated with acetic anhydride (5 ml) for 90 minutes at room temperature. Evaporation of the reaction mixture and several coevaporations with toluene give a solid that is crystallized from methanol-diethyl ether to afford pure benzyl 2-acetamido-4-O-(2-acetamido-2-deoxy-$\beta$-D-glucopyranosyl)-3-O-allyl-6-O-benzyl-2-deoxy-$\alpha$-D-glucopyranoside; yield 452 mg, m.p. 268°–270° (dec.), $[\alpha]_D^{25}+73°$ (c, 1.2, methanol). The 300-MHz nmr spectrum in methanol-d$_4$ is in accord with the desired structure.

Step C: Preparation of benzyl 2-acetamido-4-O-(2-acetamido-3,4,6-tri-O-benzyl-2-deoxy-$\beta$-D-glucopyranosyl)-3-O-allyl-6-O-benzyl-2-deoxy-$\alpha$-D-glucopyranoside To a solution of benzyl 2-acetamido-4-O-(2-acetamido-2-deoxy-$\beta$-D-glucopyranosyl)-3-O-allyl-6-O-benzyl-2-deoxy-$\alpha$-D-glucopyranoside (624 mg, 0.97 mmol) in N,N-dimethylformamide (15 ml) are added barium oxide (670 mg), barium hydroxide octahydrate (223 mg), and benzyl bromide (1.04 ml, 8.74 mmol). The reaction mixture is stirred for 20 hours at room temperature at which time additional barium oxide (335 mg), barium hydroxide octahydrate (112 mg) and benzyl bromide (0.52 ml) are added. Stirring is continued for 24 hours at room temperature. The reaction mixture is then diluted with chloroform (100 ml), washed successively with 60% aqueous acetic acid, saturated sodium bicarbonate, and water, dried (sodium sulfate), and evaporated. The residue is applied to a column of silica gel (90 g) that is eluted with 4:1 chloroform-ethyl acetate. Combination and evaporation of the appropriate fractions affords benzyl 2-acetamido-4-O-(2-acetamido-3,4,6-tri-O-benzyl-2-deoxy-$\beta$-D-glucopyranosyl)-3-O-allyl-6-O-benzyl-2-deoxy-$\alpha$-D-glucopyranoside as a white solid; yield 612 mg (69%), $[\alpha]_D^{25}+58°$ (c, 1.1, chloroform). The 300 MHz nmr spectrum in chloroform-d is in accord with the desired structure.

Step D: Preparation of benzyl 2-acetamido-4-O-(2-acetamido-3,4,6-tri-O-benzyl-2-deoxy-$\beta$-D-glucopyranosyl)-6-O-benzyl-2-deoxy-$\alpha$-D-glucopyranoside To a solution of benzyl 2-acetamido-4-O-(2-acetamido-3,4,6-tri-O-benzyl-2-deoxy-$\beta$-D-glucopyranosyl)-3-O-allyl-6-O-benzyl-2-deoxy-$\alpha$-D-glucopyranoside (597 mg, 0.65 mmol) in 7:3:1 (v/v/v) ethanol-toluene-water (25 ml) stirred at reflux temperature under an atmosphere of nitrogen are added 1,4-diazabicyclo[2.2.2] octane (75 mg, 0.67 mmol) and tris(triphenylphosphine) rhodium (I) chloride (50 mg). Two further additions of 50 mg of the rhodium catalyst are made at 90 minute intervals, and stirring at reflux temperature under nitrogen is continued overnight. The cooled solution is then evaporated, the residue taken up in chloroform (80 ml), washed three times with water, dried (magnesium sulfate), and evaporated. The residue is then stirred in aqueous (1.5 ml) tetrahydrofuran (15 ml) in the presence of mercuric chloride (750 mg) for 30 minutes at room temperature. The reaction mixture is then evaporated, the residue taken up in chloroform (75 ml), washed twice with 2.5 M aqueous potassium iodide, dried (magnesium sulfate) and evaporated to a residue that is applied to a column of silica gel (40 g) that is eluted with 2:1 chloroform-ethyl acetate. Combination and evaporation of the appropriate fractions affords benzyl 2-acetamido-4-O-(2-acetamido-3,4,6-tri-O-benzyl-2-deoxy-$\beta$-D-glucopyranosyl)-6-O-benzyl-2-deoxy-$\alpha$-D-glucopyranoside; yield 362 mg (63%); m.p. 220.5°–221.5° (methanol), $[\alpha]_D^{25}+74°$ (c, 1.5, chloroform). The 300 MHz nmr spectrum in chloroform-d is in accord with the desired structure.

Step E: Preparation of benzyl 2-acetamido-4-O-(2-acetamido-3,4,6-tri-O-benzyl-2-deoxy-$\beta$-D-glucopyranosyl)-6-O-benzyl-3-O-(D-1-carboxyethyl)-2-deoxy-$\alpha$-D-glucopyranoside To a stirred solution of benzyl 2-acetamido-4-O-(2-acetamido-3,4,6-tri-O-benzyl-2-deoxy-$\beta$-D-glucopyranosyl)-6-O-benzyl-2-deoxy-$\alpha$-D-glucopyranoside (305 mg, 0.35 mmol) in dry p-dioxane (12 ml) is added sodium hydride in oil suspension (150 mg) (50% of sodium hydride by weight). The mixture is stirred for 1 hour at 95°, the temperature decreased to 65°, and a solution of L-2-chloropropionic acid (110 mg, 1.0 mmol) in a small volume of p-dioxane is added. After 2 hours at 65°, additional sodium hydride (100 mg) is added, and the stirring is continued for 2 hours at 65°. To the cooled reaction mixture, water (10 ml) is carefully added dropwise to destroy excess sodium hydride. The mixture is concentrated, diluted to 20 ml with water, and extracted with chloroform (25 ml). The organic layer is evaporated and the residue stirred in water (30 ml) The aqueous mixture is acidified at 0° with 2.5 M hydrochloric acid to pH 3. The resulting solid is filtered and dried in vacuo over phosphorus pentoxide to give benzyl 2-acetamido-4-O-(2-acetamido-3,4,6-tri-O-benzyl-2-deoxy-$\beta$-D-glucopyranosyl)-6-O-benzyl-3-O-(D-1-carboxyethyl)-2-deoxy-$\alpha$-D-glucopyranoside as an amorphous solid; yield 286 mg (86%), $[\alpha]_D^{25}+43°$ (c, 1.2, chloroform). The 300 MHz nmr spectrum in DMSO-d$_6$ is in accord with the desired structure.

Step F: Preparation of benzyl 2-acetamido-4-O-(2-acetamido-3,4,6-tri-O-benzyl-2-deoxy-β-D-glucopyranosyl)-6-O-benzyl-2-deoxy-3-O-(D-2-propionyl-L-alanyl-D-isoglutamine benzyl ester)-α-D-glucopyranoside To a solution of benzyl 2-acetamido-4-O-(2-acetamido-3,4,6-tri-O-benzyl-2-deoxy-β-D-glucopyranosyl)-6-O-benzyl-3-O-(D-1-carboxyethyl)-2-deoxy-α-D-glucopyranoside (93.6 ml, 0.099 mmol) in dry N,N-dimethylformamide (3 ml) at −15° are added successively N-methylmorpholine (12 μl) and isobutyl chloroformate (13.5 μl). After stirring 15 minutes at −15°, a precooled solution of L-alanyl-D-isoglutamine benzyl ester hydrochloride (44.9 mg, 0.13 mmol) and N-methylmorpholine (16 μl) in dry N,N-dimethylformamide (3 ml) is added. The reaction mixture is then stirred for 2½ hours at −15° with exclusion of moisture. After the temperature is increased to 0°, 2.5 M aqueous potassium hydrogen carbonate (2 ml) is added, and the mixture is stirred for 30 minutes at 0° and then poured into water (70 ml). The precipitated solid is filtered, washed with water, dried by suction and in vacuo over phosphorus pentoxide at 50°; yield 103 mg (84%), m.p. 214°–216° (dec.), $[\alpha]_D^{25}+35°$ (c, 1, chloroform). The 300 MHz nmr spectrum in DMSO-$d_6$ is in accord with the desired structure.

Step G: Preparation of 2-acetamido-4-O-(2-acetamido-2-deoxy-β-D-glucopyranosyl)-3-O-(D-2-propionyl-L-alanyl-D-isoglutamine)-D-glucopyranose A solution of benzyl 2-acetamido-4-O-(2-acetamido-3,4,6-tri-O-benzyl-2-deoxy-β-D-glucopyranosyl)-6-O-benzyl-2-deoxy-3-O-(D-2-propionyl-L-alanyl-D-isoglutamine benzyl ester)-α-D-glucopyranoside (64 mg) in glacial acetic acid (4 ml) is hydrogenolyzed at atmospheric pressure in the presence of palladium black (60 mg) for 48 hours at room temperature. The catalyst is removed by filtration through Celite and washed with acetic acid. The combined filtrates are evaporated, co-evaporated several times with water, and finally several times with toluene. The residue is dissolved in a small volume of methanol and the product precipitated by the addition of diethyl ether. The solid is filtered, dissolved in a small volume of water and lyophilized to afford 2-acetamido-4-O-(2-acetamido-2-deoxy-β-D-glucopyranosyl)-2-deoxy-3-O-(D-2-propionyl-L-alanyl-D-isoglutamine)-D-glucopyranose as a white amorphous solid; yield 34 mg, 94%. The 300 MHz nmr spectrum in deuterium oxide is in accord with the desired structure.

EXAMPLE 4

This example shows the use of the adjuvants of the present invention in formulating influenza vaccines. An aqueous suspension of the final product of the example indicated in Column I in phosphate buffered saline is added in the level indicated in column II to a sample of bivalent whole influenza vaccine having the total amount of antigen indicated in column III. The total volume of the completed vaccine is shown in column IV.

| I | II (mg) | III (mg) | IV (ml) |
|---|---------|----------|---------|
| 1 | 0.001   | 0.01     | 0.25    |
| 1 | 0.005   | 0.05     | 0.5     |

-continued

| I  | II (mg) | III (mg) | IV (ml) |
|----|---------|----------|---------|
| 1  | 0.01    | 0.1      | 0.75    |
| 1  | 0.05    | 0.3      | 0.25    |
| 1  | 0.1     | 0.5      | 0.5     |
| 2  | 0.001   | 0.01     | 0.75    |
| 2  | 0.005   | 0.05     | 0.25    |
| 2  | 0.01    | 0.1      | 0.5     |
| 2  | 0.05    | 0.3      | 0.75    |
| 2  | 0.1     | 0.5      | 0.25    |
| 2  | 0.001   | 0.01     | 0.5     |
| 3  | 0.005   | 0.05     | 0.75    |
| 3  | 0.01    | 0.1      | 0.25    |
| 3  | 0.05    | 0.30     | 0.5     |
| 3  | 0.1     | 0.5      | 0.75    |

EXAMPLE 5

A group of 10 mice are injected with 0.1 ml of a saline solution containing 100 μg of the compound of Example 1. Seven days later the mice are challenged with a lethal dose of meningococcal B protein and meningococcal polysaccharides types A and B in 5% hog gastric mucin. In replicate tests the survival rate 72 hours post challenge is from 40–50%. Similar results are obtained with the compounds of Examples 2 and 3.

What is claimed is:

1. A 2-amino-2-deoxy-β-D-glucopyranosyl-(1→4)-2-amino-2-deoxy-D-glucose of the general structural formula:

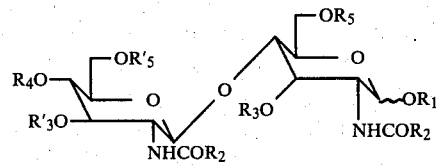

wherein
$R_1$ is hydrogen, alkyl (1–7C), substituted alkyl (1–7C) wherein the substituent is hydroxy, mercapto, alkoxy of 1–3 carbons, alkyl mercapto of 1–3 carbons, hydroxy or mercapto esterified by an acid of 1–4 carbon atoms, F, Cl, Br, carboxyl, or carboxyl functionally modified by esterification with an alcohol of 1–3 carbons or by amidation, phenyl, substituted phenyl wherein the substituent is an alkyl group of 1–3 carbons, hydroxy, mercapto, hydroxy or mercapto etherified by an alkyl group of 1–3 carbons, hydroxy or mercapto esterified by an acid of 1–4 carbons, alkyldioxy (1–4C), cycloalkyldioxy (5–7C), amino or trifluoromethyl, benzyl, or substituted benzyl wherein the substituent is an alkyl group of 1–3 carbons, hydroxy, mercapto, hydroxy or mercapto etherified by an alkyl group of 1–3 carbon atoms, hydroxy or mercapto esterified by an acid of 1–4 carbons, alkyldioxy (1–4C), cycloalkyldioxy (5–7C), amino or trifluoromethyl;

$R_2$ is alkyl (1–7C), substituted alkyl (1–7C) wherein the substituent is hydroxy, mercapto, alkoxy of 1–3 carbons, alkylmercapto of 1–3 carbons, hydroxy or mercapto esterified by an acid of 1–4 carbon atoms, F, Cl, Br, carboxyl, or carboxyl functionally modified by esterification with an alcohol of 1–3 carbons or by amidation, phenyl, or substituted phenyl wherein the substituent is an alkyl group of 1–3 carbons, hydroxy, mercapto, hydroxy or mercapto etherified by an alkyl group of 1–3 carbon atoms, hydroxy or mercapto esterified by an acid of 1-4 carbons, alkyldioxy (1-4C), cycloalkyldioxy (5-7C), amino or trifluoromethyl and each $R_2$ may be the same group or a different group;

$R_3$ and $R'_3$ are H or $$R_8-\underset{I}{\overset{O}{\overset{\|}{C}H}}-\overset{R_9}{\overset{|}{C}}-\overset{R_{10}}{\overset{|}{N}}-\underset{II}{\overset{O}{\overset{\|}{C}H}}-\overset{}{\overset{}{C}}-NH-\underset{III}{\overset{R_{11}}{\overset{|}{C}H}}-(CH_2)_2-R_{12}$$

wherein $R_8$ is H or lower alkyl (1-10C), and provided at least one of $R_3$ and $R'_3$ is not H;

$R_9$ is H, or $R_9$-$R_{10}$ together is $-CH_2CH_2CH_2-$;

$R_{10}$ is H, alkyl (1-7C) hydroxymethyl, mercaptomethyl, benzyl, or substituted benzyl wherein the substituent is an alkyl group of 1-3 carbon atoms, hydroxy, mercapto, hydroxy or mercapto etherified by an alkyl group of 1-3 carbons, hydroxy or mercapto esterified by an acid of 1-4 carbons, alkyldioxy (1-4C), cycloalkyldioxy (5-7C), amino or trifluoromethyl;

$R_{11}$ and $R_{12}$ each are independently carboxyl, esterified carboxyl (1-7C), amidated carboxyl, or mono- or di-alkyl (1-7C) amidated carboxyl;

$R_4$, $R_5$ and $R'_5$ are the same or different and are H, aliphatic or aromatic acyl (2-21C) or substituted acyl (2-21C) wherein the substituent is halogen, alkyl (1-3C), alkoxy (1-3C), trifluoromethyl, hydroxy, alkanoyloxy (1-3C), provided when $R_8$ is loweralkyl, the stereo chemistry at asymmetric center I can be either $\underline{D}$ or $\underline{L}$; and when $R_{10}$ is not H, the stereochemistry at asymmetric center II is $\underline{L}$; the stereochemistry at asymmetric center III is $\underline{D}$;

provided further when $R_1$, $R_5$, $R'_3$, $R_4$, and $R'_5$ are each H and each $R_2$ is $CH_3$, $R_3$ is not $H_3CCHCOR_{13}$ wherein $R_{13}$ is a dipeptide.

2. A compound of claim 1 wherein $R_2$ is methyl.

3. A compound of claim 1 wherein $R_1$ and $R_5$ are hydrogen, and $R_4$ and $R'_5$ are hydrogen or acetyl.

4. A compound of claim 1 wherein $R_3$ and $R'_3$ are H or $$HC-\overset{O}{\overset{\|}{C}}-\overset{H}{\overset{|}{N}}-\overset{CH_3}{\overset{|}{CH}}-\overset{O}{\overset{\|}{C}}-\overset{H}{\overset{|}{N}}-\overset{H}{\overset{|}{C}}-CONH_2$$
$$H_3C \qquad\qquad\qquad CH_2CH_2CO_2H.$$
$$\underline{D} \qquad\qquad \underline{L} \qquad\qquad \underline{D}$$

5. A compound of claim 2 wherein $R_1$, $R_3$, $R_4$, $R'_5$ and $R_5$ are hydrogen and $R'_3$ is $$HC-\overset{O}{\overset{\|}{C}}-\overset{H}{\overset{|}{N}}-\overset{CH_3}{\overset{|}{CH}}-\overset{O}{\overset{\|}{C}}-\overset{H}{\overset{|}{N}}-\overset{H}{\overset{|}{C}}-CONH_2$$
$$H_3C \qquad\qquad\qquad CH_2CH_2CO_2H.$$
$$\underline{D} \qquad\qquad \underline{L} \qquad\qquad \underline{D}$$

6. A compound of claim 2 wherein $R_1$ and $R_3$ and $R_5$ are hydrogen, $R_4$ and $R'_5$ are acetyl and $R'_3$ is $$HC-\overset{O}{\overset{\|}{C}}-\overset{H}{\overset{|}{N}}-\overset{CH_3}{\overset{|}{CH}}-\overset{O}{\overset{\|}{C}}-\overset{H}{\overset{|}{N}}-\overset{H}{\overset{|}{C}}-CONH_2$$
$$H_3C \qquad\qquad\qquad CH_2CH_2CO_2H.$$
$$\underline{D} \qquad\qquad \underline{L} \qquad\qquad \underline{D}$$

7. A compound of claim 2 wherein $R_1$ $R'_3$, $R_4$, $R'_5$ and $R_5$ are hydrogen and $R_3$ is $$HC-\overset{O}{\overset{\|}{C}}-\overset{H}{\overset{|}{N}}-\overset{CH_3}{\overset{|}{CH}}-\overset{O}{\overset{\|}{C}}-\overset{H}{\overset{|}{N}}-\overset{H}{\overset{|}{C}}-CONH_2$$
$$H_3C \qquad\qquad\qquad CH_2CH_2CO_2H$$
$$\underline{D} \qquad\qquad \underline{L} \qquad\qquad \underline{D}$$

8. A compound of claim 1 wherein $R_1$ is H, alkyl of 1-3 carbons, benzyl, phenyl or phenyl p-substituted by alkyl (1-3C), amino, F, Cl, Br, hydroxy or trifluoromethyl; $R_2$ is alkyl of 1-3 carbons, or phenyl, or phenyl p-substituted by alkyl (1-3C), amino, F, Cl, Br, hydroxy or trifluoromethyl; $R_3$ is H, $R_4$ and $R_5$ are H, alkanoyl of 2-21 carbons, benzoyl or naphthoyl; $R_{10}$ is H, alkyl or 1-4 carbons, hydroxymethyl, mercaptomethyl, benzyl or p-hydroxybenzyl; $R_9$ and $R_{10}$ together are $-CH_2CH_2CH_2-$; and $R_{11}$ and $R_{12}$ are carboxyl, carboxyl esterified by an alcohol of 1-4 carbons, carboxamide, or monoalkyl or dialkyl substituted carboxamide wherein the alkyl group has from 1-3 carbons.

9. Compounds of the formula wherein

Ac is a residue of an aliphatic carboxylic acid having at least 3 carbon atoms; and R is a dipeptide.

10. A composition having immunostimulatory properties comprising a compound of claim 1 in an amount effective to produce an immunostimulatory effect and a pharmaceutically acceptable carrier.

11. An antibacterial composition comprising a compound of claim 1 in an amount effective to produce an antibacterial effect and a physiologically acceptable medium.

12. A composition of claim 10 in aqueous formulation.

13. A composition of claim 10 in oil formulation.

* * * * *